United States Patent [19]

Hoult

[11] Patent Number: 5,077,481
[45] Date of Patent: Dec. 31, 1991

[54] OPTICAL PROBE FOR MEASURING LIGHT TRANSMISSION OF LIQUID

[75] Inventor: Robert A. Hoult, Bethel, Conn.

[73] Assignee: The Perkin-Elmer Corporation, Norwalk, Conn.

[21] Appl. No.: 603,593

[22] Filed: Oct. 25, 1990

[51] Int. Cl.$^5$ ............................................. G01N 15/06
[52] U.S. Cl. ..................................... 250/576; 356/246
[58] Field of Search ............... 250/573, 574, 575, 576; 356/246, 404, 405, 406

[56] References Cited

U.S. PATENT DOCUMENTS

| | | |
|---|---|---|
| 4,222,670 | 9/1980 | Koshiishi . |
| 4,229,179 | 10/1980 | Lee . |
| 4,403,861 | 9/1983 | Boisde et al. . |
| 4,431,307 | 2/1984 | Suovaniemi . |
| 4,749,276 | 6/1988 | Bragg et al. ........................ 356/246 |
| 4,872,753 | 10/1989 | Danigel ............................... 250/576 |

Primary Examiner—David C. Nelms
Attorney, Agent, or Firm—H. S. Ingham; E. T. Grimes

[57] ABSTRACT

An optical probe is for measurement of light transmission of liquid. A tubular housing three equally configured legs defining three arcuately spaced openings in the housing wall. A solid cylindrical member formed of glass or fused silica has a flat transparent end surface and an opposing curved surface silvered to form an internally concave reflector. The cylindrical member is retained in the housing with the transparent end surface adjacent to the openings. A transparent rod member has a flat first end surface and a flat second end surface parallel to the first end surface. The rod member is retained in the housing with the second end surface adjacent to the openings and spaced from the transparent end surface parallel thereto so as to define a cavity therebetween such that, upon immersion of the probe, liquid passes through the openings into the cavity. The first end surface is spaced from the concave reflector so that conjugate focal spots of the concave reflector are located at the first end surface. Two first optical fibers are affixed respectively to the focal spots. Light entering through one optical fiber passes twice through the liquid in the opening while being reflected by the concave reflector into the other optical fiber.

8 Claims, 1 Drawing Sheet

OPTICAL PROBE FOR MEASURING LIGHT TRANSMISSION OF LIQUID

This invention relates to measuring light transmission of liquids, and particularly to an optical probe for immersion into liquids for measurement.

BACKGROUND OF THE INVENTION

One conventional class of spectrophotometers is utilized for measuring optical transmission of liquid samples in the spectral range of near infrared to ultraviolet. There are continuing needs for improvements in precision and in ease of incorporating the optics of the instrument into each of a set of sample liquids. Precision in measurements is particularly related to uniformity in pathlength in the optical train at the liquid sample, and minimizing reflection and refraction effects. Mechanically, an optical probe device should be small, portable, reliable and rugged. Fiber optics provide a basis for a suitable probe that may be inserted into liquid samples.

The usual way to sample any one of a number of liquids contained in separate containers is to aspirate the selected liquid from its container into the instrument. Typical examples are described in U.S. Pat. Nos. 4,229,179 (Lee) and 4,222,670 (Koshiishi). The latter patent also illustrates concerns for precision optical surfaces in the system for measuring light transmission of the liquid, and for removing liquid from the optical system in preparation for the next sample. Generally the aspiration method adds time to the process and requires significant channeling susceptible of contamination by prior liquids.

U.S. Pat. No. 4,431,307 (Suovanieme) teaches arranging the liquid containers ("cuvettes") in a matrix, with each container having its own optics. The use of optical fibers immersed in liquid is disclosed in U.S. Pat. No. 4,403,861 (Boisde et al), apparently with a simple gap between fiber ends for passing light through a portion of the liquid This approach potentially solves some of the above problems but does not address any need or method for incorporating precision optics into the liquid.

An object of the invention is to provide a novel optical probe for insertion into liquids for measurement of light transmission characteristics of the liquid by a photospectrometer. A further object is to provide such an optical probe having improved optical precision. Another object is to provide such a probe that is small, portable, reliable and rugged.

SUMMARY OF THE INVENTION

The foregoing and other objects are achieved by an optical probe including a tubular housing with a cylindrical wall having one or more proximate openings therein. A solid cylindrical member is formed of transparent material with a flat transparent end surface and an opposing curved surface having a selected curvature and being silvered so as to form an internally concave reflector. The cylindrical member is retained in the housing with the transparent end surface located adjacent to the openings.

A transparent solid rod member has a flat first end surface and a flat second end surface parallel to the first end surface. The rod member is retained in the housing with the second end surface located adjacent to the openings and spaced from the transparent end surface parallel thereto so as to define a cavity therebetween.

Upon immersion of the probe, liquid passes through the openings into the cavity. The first end surface is spaced from the concave reflector cooperatively with the selected curvature, the cavity and indices of refraction of the reflector member, the rod member and the liquid so that selected first and second conjugate focal spots of the concave reflector are located in a laterally spaced relationship substantially at the first end surface.

A first optical fiber with a planar end is affixed transparently to the first end surface in alignment with the first focal spot, and a second optical fiber with a planar end is affixed transparently to the first end surface in alignment with the second focal spot.

Light entering through the first optical fiber thereby passes twice through the liquid in the opening while being reflected by the concave reflector into the second optical fiber with minimal refraction and reflection losses.

In a preferred aspect the cylindrical wall proximate the cavity comprises three equally configured legs so that the openings are configured as three arcuately spaced openings to the cavity. Also the cylindrical member and the rod member should have respective cylindrical surfaces blackened against extraneous reflections.

DETAILED DESCRIPTION OF THE INVENTION

Figures 1, 2:
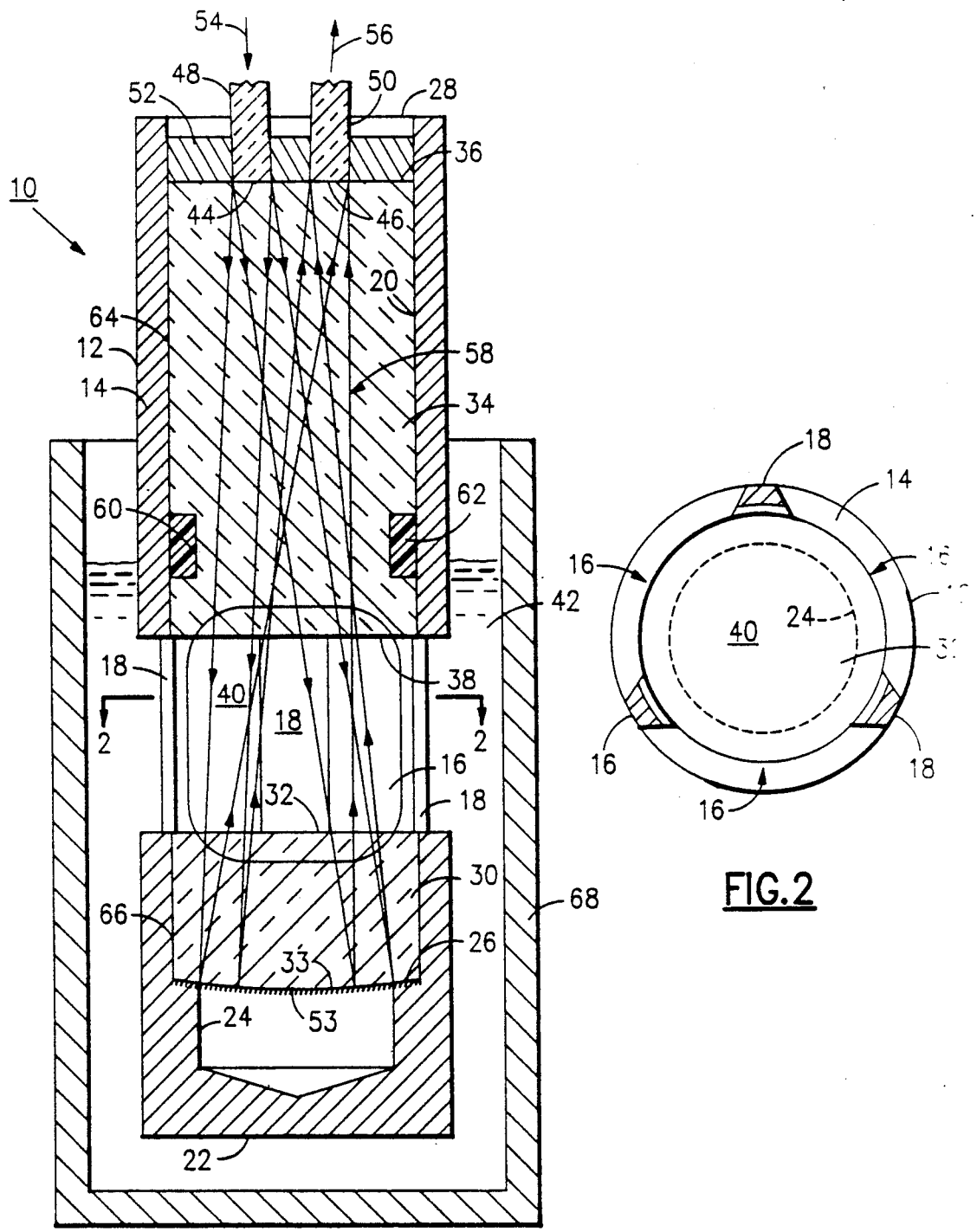
FIG. 1 is a longitudinal section of an optical probe according to the invention.
FIG. 2 is a cross section taken at 2—2 of FIG. 1.

With reference to FIG. 1, an optical probe 10 includes a tubular housing 12 with a cylindrical wall 14 of stainless steel having three equal and arcuately spaced proximate openings 16 therein. These openings are formed conveniently with the cylindrical wall having a portion configured with three equally spaced legs 18, as shown in cross section in FIG. 2. The housing otherwise has a uniform inside diameter 20 except for a bottom end 22 that may have a lesser diameter 24 to form an annular shoulder 26. That bottom may be closed but the other end 28 is open.

A solid cylindrical member 30 is made of glass or fused quartz or other transparent material. This member is bonded by a flat transparent end surface 32 and an opposite curved surface 33. The curved surface is silvered with aluminum or the like and has a selected curvature so as to form an internally concave reflector. The member 30 is retained in the housing 12 with cement against the shoulder 26 with the transparent surface adjacent to the openings 16.

A transparent solid rod member 34 has a flat first end surface 36 and a flat second end surface 38 parallel to the first end surface. These end surfaces, as well as the transparent surface 32 of the cylindrical member 30, are polished and accurately parallel to each other. The rod member 34 is retained with cement in the housing 12 with the second end surface 38 adjacent to the openings 16 and spaced from the transparent surface 32 to define a cavity 40 therebetween. The cavity is directly accessed through the openings 16 so that upon immersion of the probe into a liquid 42, the liquid passes through the openings into the cavity. There may be only one or any reasonable number of openings, so long as there is reasonable access and egress for the liquid to the cavity. The three legs 18 and openings 16 provide for good support and easy access to the chamber for cleaning. Also, as shown, the openings may extend over the transparent members 30,34.

The first end surface 36 is spaced from the concave reflector 33 at a distance selected cooperatively with the selected curvature and with indices of refraction of the reflector member, the rod member and the liquid, such that selected first and second conjugate focal spots 44,46 of the concave reflector 33 are positioned in laterally spaced relationship at the first end surface 36.

A first optical fiber 48 with a flat end is affixed transparently to the first end surface 36 in alignment with the first focal spot 44. A second optical fiber 50 with a flat end is affixed similarly to the first end surface 52 in alignment with the second focal spot 46. Strength and rigidity may be achieved by first affixing the fibers through holes in a disk 52 cemented into the housing 14 contacting end surface 36. The flat ends of the fibers may be polished in the disk before attachment. The fibers at the disk each should be angled so as to aim at the optical center 53 of the reflective surface 33.

Light 54 entering through the first optical fiber 48 passes progressively through the rod 34, the liquid 42 in the chamber 40 and the cylindrical member 30 The light then is reflected by the concave reflector back through the train of the member, liquid and rod into the second optical fiber 50 as output light 56. The light rays in the probe 10 are shown generally by path lines 58. Thus the light beam passes twice through the liquid 42 in the cavity 40, on entry and return, doubling any light absorption by the liquid Transmission characteristics of the liquid can thereby be measured with a spectrophotometer instrument (not shown) coupled with the optical fibers, by conventionally comparing the output light to the input light. Advantageously the rod member 34 has an annular groove 60 therein for defining an optical aperture for the light. This also provides an anchoring location for cement 62.

With the configuration of the probe of the invention a high degree of precision is achieved with a uniform pathlength of the light passing through the liquid. Refraction and reflection losses are minimized in the disclosed configuration of the probe, the parallel surfaces and, with elimination of air from the optical train, a similarity of indices of refraction of glass or quartz and most liquids. For greater precision a glass may be selected having an index of refraction substantially the same as that of the intended liquid. Also the cylindrical member 30 and the rod member 34 preferably have their respective cylindrical boundary surfaces 64,66 blackened against extraneous reflections, further improving performance.

The probe is quite rugged. Suitable dimensions for the probe are 8 mm outside diameter and about 2.5 cm long, excluding the extension of the optical fibers. Such size is convenient for insertion into liquid sample cups 68 conventionally used for spectrophotometers.

While the invention has been described above in detail with reference to specific embodiments, various changes and modifications which fall within the spirit of the invention and scope of the appended claims will become apparent to those skilled in this art. Therefore, the invention is intended only to be limited by the appended claims or their equivalents.

What is claimed is:

1. An optical probe useful for measurement of light transmission of liquid, comprising:
   a tubular housing with a cylindrical wall having one or more proximate openings therein;
   a solid cylindrical member formed of transparent material with a flat transparent end surface and an opposing curved surface having a selected curvature and being silvered so as to form an internally concave reflector, the cylindrical member being retained in the housing with the transparent end surface located adjacent to the openings;
   a transparent solid rod member with a flat first end surface and a flat second end surface parallel to the first end surface, the rod member being retained in the housing with the second end surface located adjacent to the openings and spaced from the transparent end surface parallel thereto so as to define a cavity therebetween such that, upon immersion of the probe, liquid passes through the openings into the cavity, the first end surface being spaced from the concave reflector cooperatively with the selected curvature, the cavity and indices of refraction of the reflector member, the rod member and the liquid so that selected first and second conjugate focal spots of the concave reflector are located in laterally spaced positions substantially at the first end surface;
   a first optical fiber with a planar end affixed transparently to the first end surface in alignment with the first focal spot; and
   a second optical fiber with a planar end affixed transparently to the first end surface in alignment with the second focal spot;
   whereby light entering the rod member from the first optical fiber passes twice through the liquid in the opening while being reflected by the concave reflector into the second optical fiber.

2. The probe according to claim 1 wherein the rod member has an annular groove therein defining an optical aperture for the light.

3. The probe according to claim 1 wherein the cylindrical wall has three proximate openings therein.

4. The probe according to claim 3 wherein the cylindrical wall proximate the cavity comprises three equally configured legs so that the openings are configured as three arcuately spaced openings to the cavity.

5. The probe according to claim 1 wherein the cylindrical member and the rod member have respective cylindrical surfaces blackened against extraneous reflections.

6. The probe according to claim 1 wherein the cylindrical member and the rod member are formed of glass or fused silica.

7. The probe according to claim 1 wherein the indices of refraction of the cylindrical member and the tubular member are substantially the same as that of the liquid.

8. The probe according to claim 1 wherein the concave reflector has an optical center and the optical fibers are each angled so as to aim at the optical center.

* * * * *